United States Patent [19]

Torii et al.

[11] Patent Number: 4,886,891

[45] Date of Patent: Dec. 12, 1989

[54] PROCESS FOR PREPARING 1,1-DISUBSTITUTED ETHYLENE DERIVATIVE BY REACTION OF LEAD WITH A CARBINOL DERIVATIVE

[75] Inventors: Shigeru Torii, Okayama; Masatoshi Taniguchi, Tokushima; Michio Sasaoka, Tokushima; Yoshihisa Tomotaki, Tokushima; Mitsuo Akada, Tokushima; Hideo Tanaka, Okayama; Akira Suzuki; Shiro Yamashita, both of Kurashiki, all of Japan

[73] Assignee: Otsuka Kagaku Kabushiki Kaisha, Osaka, Japan

[21] Appl. No.: 134,852

[22] Filed: Dec. 18, 1987

[30] Foreign Application Priority Data

Dec. 20, 1986 [JP] Japan .................................. 61-304810
Mar. 6, 1987 [JP] Japan .................................. 62-52625

[51] Int. Cl.$^4$ ........................................... C07C 37/00
[52] U.S. Cl. .................... 549/434; 534/584; 549/445; 558/379; 558/383; 558/401; 558/423; 558/425; 558/434; 560/104; 560/128; 560/211; 560/214; 562/599; 564/182; 568/338; 568/364; 568/376; 568/407; 568/631; 568/648; 568/654; 568/765; 568/772; 568/774; 568/908; 570/182; 570/183; 570/190; 570/193; 570/200; 570/216; 570/218; 570/226; 570/227; 570/230

[58] Field of Search ........................ 534/584; 437/945; 549/434, 445; 558/379, 383, 401, 423, 425, 434; 560/104, 128, 211, 214; 562/599; 564/182; 568/338, 364, 376, 407, 631, 648, 657, 765, 772, 774, 908; 570/182, 183, 190, 193, 200, 216, 218, 226, 227, 230

[56] References Cited

PUBLICATIONS

Fujita et al, Tetrahedron Letters, vol. 27, pp. 2139 to 2141 (1986).
Rabjohn et al, "Organic Syntheses", Collective vol. 4, pp. 268 to 270 (1963).
Schwarz et al, Chemical Abstracts, vol. 101, #130888k (1984).

*Primary Examiner*—Floyd D. Higel
*Attorney, Agent, or Firm*—Larson and Taylor

[57] ABSTRACT

The present invention provides a process for preparing a 1,1-disubstituted ethylene derivative of the formula

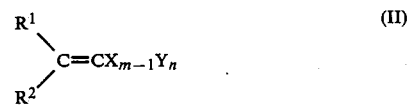

which comprises reacting lead with a carbinol derivative of the formula

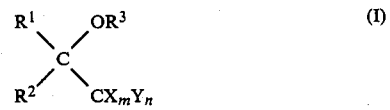

wherein $R^1$, $R^2$, $R^3$, X, Y, m and n are defined in the specification. The reaction is conducted more advantageously in the presence of a metal having higher ionization tendency than lead.

8 Claims, No Drawings

PROCESS FOR PREPARING 1,1-DISUBSTITUTED ETHYLENE DERIVATIVE BY REACTION OF LEAD WITH A CARBINOL DERIVATIVE

The present invention relates to novel processes for preparing a 1,1-disubstituted ethylene derivative.

Conventionally, the following methods have been known to prepare a 1,1-disubstituted ethylene derivative of the formula (II) from a carbinol derivative of the formula (I).

A method of using zinc with an excess amount than the stoichiometric amount (Japan Kokai No. 93089/1984, Japan Kokoku No. 30301/1985, Tetrahedron Letters, 27, 2139 (1986), Tetrahedron Letters, 27, 3655 (1986).

An electrolysis method [Angew. Chem. Int. Ed. Engl., 16, 57 (1977), Japan Kokai Nos. 52236/1983 and 144487/1983].

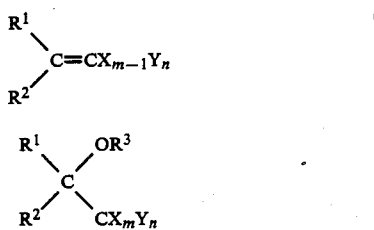

wherein $R^1$ and $R^2$ are same or different and are each hydrogen atom, $C_1 \sim C_{10}$ straight-chain or branched-chain alkyl group, $C_3 \sim C_{10}$ alicyclic group, $C_3 \sim C_{10}$ alicyclic group having at least one side chain having 1 to 5 carbon atoms, $C_2 \sim C_{10}$ straight-chain or branched-chain unsaturated hydrocarbon group, aryl group, heterocyclic group, aralkyl group or aryloxy group, $R^1$ and/or $R^2$ may form a ring together with a carbon chain with or without containing a heteroatom(s). $R^1$ and $R^2$ may have a substituent(s) selected from the group consisting of hydroxyl group, protected hydroxyl group, acyl group, acyloxy group, halogen atom, $C_1 \sim C_5$ straight-chain or branched-chain alkyl group, $C_2 \sim C_6$ straight-chain or branched-chain unsaturated hydrocarbon group, aralkyl group, amino group, amino group substituted by $C_1 \sim C_5$ straight-chain or branched-chain alkyl group, protected amino group, nitro group, protected thiol group, carboxyl group, protected carboxyl group, formyl group, protected formyl group, sulfonic acid group, protected sulfonic acid group and cyano group. The substituents are one to five in number and are same or different each other. One to three of —$CH_2$— groups in $R^1$ or $R^2$ may be replaced by —CO— group. $R^3$ is hydrogen atom, $C_1 \sim C_5$ straight-chain or branched-chain alkyl group, substituted or unsubstituted aryl group, aralkyl group having a substituted or unsubstituted aryl group(s), acyl group or —$(CH_2)_j$— group bonded to $R^1$ in one terminal, j=0~5, a part of —$(CH_2)_j$— group may be —CO— group. X and Y are same or different and are fluorine, chlorine, bromine or iodine atom, m and n are an integer of 1 to 2, m+n=3, when m is 2, Y may be further hydrogen atom, carboxyl group, protected carboxyl group, amido group, cyano group or trifluoromethyl group.

However, these methods inevitably produce by-products which cause to lower reaction selectivity and give adverse effects on the purification of the desired 1,1-disubstituted ethylene derivative. Further, the former methods require heavy metals in an amount more than the stoichiometric amount which bring a lot of problems in public pollution and cause a problem in industrial application. The latter electrolytic method has defects of using a special apparatus which renders the method less popular and of being not easy in maintenance of the equipment.

An object of the invention is to provide processes for preparing a 1,1-disubstituted ethylene derivative of the above formula (II) which are free from the above conventional drawbacks and are conducted with a safe and simple procedure with industrial advantages.

The above and other objects of the invention will become apparent from the following description.

The present invention provides a process for preparing a 1,1-disubstituted ethylene derivative of the formula

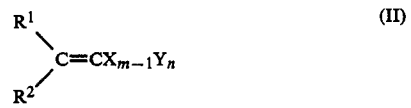

which comprises reacting lead with a carbinol derivative of the formula

wherein $R^1$, $R^2$, $R^3$, X, Y, m and n are same as above.

The 1,1-disubstituted ethylene derivative of the formula (II) obtained in the present invention is an important compound as an intermediate for pharmaceuticals, agricultural chemicals, etc. For example, from the compound (II) are obtained chrysanthemumic acid derivatives which are starting materials of pyrethroid insecticides. Further in case $R^1$ is aryl group and X and Y are halogen atoms, the compound (II) can easily be subjected to hydrolysis to obtain aryl acetic acid derivatives which are useful as a starting material of antibiotics, β-blockers, anti-inflammatory agents, etc.

The present inventors have found and paid attention to the fact that 1,1-disubstituted ethylene derivative can be obtained in excellent selectivity only when using lead as a cathode material in the above conventional electrolytic reduction method. It is presumed that the reaction does not proceed only with direct electron transfer on the cathode and that a reaction occurs between the lead cathode and the substrate to produce 1,1-disubstituted ethylene derivative in good selectivity when the lead cathode is used.

On the other hand, conventionally, reactions of reducing organic compounds with lead are hardly known. As a few examples, reductive dimerization of butyl bromide, benzoyl chloride or benzyl chloride are reported in a low yield of about 50% in Titrahedron Letters, 4951 (1967) and reduction of aromatic nitro compounds in J. Chem. Soc., (C) 2403 (1968). For example, Fieser's Reagents for Organic Synthesis, Vol. 1~12 (A Weiley -Interscience Publication) does not disclose other examples of reactions in which lead is used as a reducing agent.

Based on the afore-mentioned consideration, the present inventors have investigated the reduction of the carbinol derivative of the formula (I), and found that lead is an excellent reducing agent for the reaction of the present invention. In the present invention, 1,1-disubstituted ethylene derivative of the formula (II) is prepared in a high yield without accompanying side-product and with a simple procedure, by reacting the carbinol derivative of the formula (I) with lead or a catalytic amount of lead or lead compound in the presence of a metal having higher ionization tendency than lead in an organic solvent or aqueous organic solvent, as required with addition of an acid.

In the invention, $R^1$ and $R^2$ are same or different and are each hydrogen atom, $C_1 \sim C_{10}$ straight-chain or branched-chain alkyl group, $C_3 \sim C_{10}$ alicyclic group, $C_3 \sim C_{10}$ alicyclic group having at least one side chain having 1 to 5 carbon atoms, $C_2 \sim C_{10}$ straight-chain or branched-chain unsaturated hydrocarbon group, aryl group, heterocyclic group, aralkyl group or aryloxy group, $R^1$ and/or $R^2$ may form a ring together with a carbon chain with or without containing a heteroatom(s). $R^1$ and $R^2$ may have a substituent(s). Examples of $C_1 \sim C_{10}$ straight-chain or branched-chain alkyl groups are methyl, ethyl, propyl, isopropyl, butyl, isobutyl, tert-butyl, amyl, isoamyl, hexyl, octyl or decyl, examples of $C_3 \sim C_{10}$ alicyclic groups are cyclopropyl, cyclobutyl, cyclopentyl, cyclohexyl, cyclooctyl, cyclodecyl, cyclobutenyl, cyclopentenyl, cyclohexenyl, cycloheptenyl, cyclooctenyl or cyclooctadienyl, examples of $C_3 \sim C_{10}$ alicyclic groups having at least one side chain having 1 to 5 carbon atoms are 1-methylcyclopropyl, 2-methylcyclopropyl, 2,2-dimethylcyclopropyl, 3-methylcyclobutyl, 1-methylcyclopentyl, 2-methylcyclopentyl, 3-methylcyclopentyl, 3-ethylcyclopentyl, 3-tert-butylcyclopentyl, 4-isopropylcyclohexyl or 4-tert-butylcyclohexyl, examples of $C_2 \sim C_{10}$ straight-chain or branched-chain unsaturated hydrocarbon groups are vinyl, ethynyl, 1-propenyl, 2-propenyl, 2-methyl-1-propenyl, 2-methyl-2-propenyl, propynyl, 3-butenyl, butynyl, pentenyl, pentadienyl, pentynyl, hexenyl, hexynyl, heptenyl, heptynyl, octenyl, octynyl, 9-decenyl, prenyl or geranyl. Aryl groups include phenyl group or polycyclic aromatic hydrocarbon groups. The latter groups include α-naphthyl, β-naphthyl, anthranyl or pyrenyl. Heterocyclic groups include cyclic groups containing oxygen, nitrogen, sulfur atom, etc. Typical examples thereof are tetrahydrofuryl, furyl, tetrahydropyranyl, pyranyl, pyrrolyl, piperidinyl, pyridyl, oxazolyl, morpholinyl, tetrahydrothienyl, thienyl, thiadiazolyl, triazolyl, thiazolyl or tetrazolyl. Examples of aralkyl groups are benzyl, phenethyl, phenylbutyl, diphenylmethyl, triphenylmethyl, naphthylmethyl or naphthylethyl, examples of aryloxy groups are phenoxy, α-naphthyloxy, β-naphthyloxy, anthranyloxy or pyrenyloxy. Further, the ring formed with a carbon chain with or without containing a heteroatom(s) is represented by [—(CH$_2$)k—] in which k is 2 to 13 and oxygen, nitrogen, sulfur or like heteroatom may be introduced in place of —CH$_2$—.

Further, substituents for the above $R^1$ and $R^2$ include hydroxyl group, protected hydroxyl group, acyl group, acyloxy group, halogen atom, $C_1 \sim C_5$ straight-chain or branched-chain alkyl group, $C_2 \sim C_6$ straight-chain or branched-chain unsaturated hydrocarbon group, aralkyl group, amino group, amino group substituted by $C_1 \sim C_5$ straight-chain or branched-chain alkyl group, protected amino group, nitro group, protected thiol group, carboxyl group, protected carboxyl group, formyl group, protected formyl group, sulfonic acid group, protected sulfonic acid group and cyano group. The substituents are one to five in number and are same or different each other. Examples of protective groups for hydroxyl group are methyl, ethyl, propyl, isopropyl, butyl and like lower alkyl groups, or protective groups for hydroxyl group described on Chapter 2 of "Protective Groups in Organic Synthesis" (A Weiley-Interscience Publication, 1981) by Theodora W. Greene. Examples of acyl groups are formyl, acetyl, propionyl, valeryl, group represented by the formula

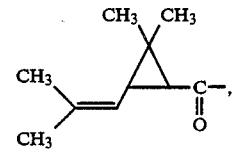

benzoyl, toluoyl or furoyl. Examples of acyloxy groups are formyloxy, acetyloxy, propionyloxy, valeryloxy, benzoyloxy, toluoyloxy or furoyloxy, examples of halogen atoms are fluorine, chlorine, bromine or iodine atom. Examples of $C_1 \sim C_5$ straight-chain or branched-chain alkyl groups are methyl, ethyl, propyl, isopropyl, butyl, tert-butyl, amyl or isoamyl. Examples of $C_2 \sim C_6$ straight-chain or branched-chain unsaturated hydrocarbon groups are vinyl, ethynyl, propenyl, butenyl or hexenyl, examples of aralkyl groups are benzyl, phenethyl, phenylpropyl, phenylbutyl or diphenylmethyl. Examples of $C_1 \sim C_5$ straight-chain or branched-chain alkyl groups which are substituents for amino group are methyl, ethyl, propyl, isopropyl, butyl, tert-butyl, amyl or isoamyl. Protective groups for amino group include those described on Chapter 7 of the above-mentioned publication. Protective groups for thiol group include methyl, ethyl, propyl, isopropyl, butyl, tert-butyl, amyl, isoamyl or like $C_1 \sim C_5$ alkyl group, phenyl, benzyl, phenethyl, and formyl, acetyl, trichloroacetyl, propionyl, benzoyl, toluoyl, furoyl or like acyl group. Protective groups for carboxyl group include those described on Chapter 5 of the above-mentioned publication. Protective groups for formyl group include those described on Chapter 4 of the above-mentioned publication. Protective groups for sulfonic acid group include methyl, ethyl, propyl, isopropyl, butyl, tert-butyl, amyl, isoamyl or like alkyl group, phenyl, benzyl, phenethyl or like aralkyl group, tetramethylammonium, tetraethylammonium, trimethylbenzylammonium or like quarternary ammonium group.

Further, one to three of —CH$_2$— groups in $R^1$ or $R^2$ may be replaced by —CO— group. Typical examples thereof are acetyl, acetonyl, 1-methyl-2-oxo-propyl, diacetylmethyl, 3-methyl-2-oxo-3-butenyl or 2-oxocyclohexyl. An example of these groups having the above-mentioned substituent is a group of the formula

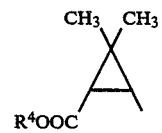

wherein $R^4$ is hydrogen atom or protective group for carboxyl group.

$R^3$ is hydrogen atom, $C_1 \sim C_5$ straight-chain or branched-chain alkyl group, substituted or unsubstituted aryl group, aralkyl group having a substituted or unsubstituted aryl group, acyl group or —$(CH_2)_j$—group bonded to $R^1$ in one terminal, $j=0\sim 5$, a part of —$(CH_2)_j$— group may be —CO— group. Examples of $C_1\sim C_5$ straight-chain or branched-chain alkyl groups are methyl, ethyl, propyl, isopropyl, butyl, tert-butyl, amyl or isoamyl. Examples of aryl groups are phenyl, α-naphthyl, β-naphthyl or anthranyl, examples of aralkyl groups are benzyl, phenethyl, phenylpropyl, phenylbutyl or diphenylmethyl. Examples of acyl groups are formyl, acetyl, trichloroacetyl, propionyl, valeryl, benzoyl, toluoyl or furoyl. These groups may have a substituent. As the substituent are shown those exemplified for $R^1$ and $R^2$. The substituents are one to five in number and are same or different each other.

X and Y are same or different and are fluorine, chlorine, bromine or iodine atom, m and n are an integer of 1 to 2, $m+n=3$, when m is 2, Y may be further hydrogen atom, carboxyl group, protected carboxyl group, amido group, cyano group or trifluoromethyl group. Examples of protective groups for carboxyl group are those described on Chapter 5 of the above-mentioned publication.

The carbinol derivative of the formula (I), the starting material of the present invention, can be prepared by the methods desclosed in Japan Kokai No. 126980/1982, Tetrahedron Letters, 22, 871 (1981), Tetrahedron Letters 1521 (1978), etc.

In the present invention, the carbinol derivative of the above formula (I) is reacted with a metal lead. The metal lead is not limited in shape and may be selected from a wide forms such as powder, plate, bulk or needle. Powdery metal lead is preferably used in order to complete the reaction at lower temperature in shorter period. The particle size of powdery metal lead is selected from a wide range but is preferably about 10 to 500 mesh. The amount of the metal lead to be used is usually about 1.0 to 10 moles atom, preferably about 1.0 to 4.0 moles atom per mole atom of the carbinol derivative of the formula (I).

In the invention, it is possible to extremely reduce the amount of the metal lead, render the waste treatment easy and conduct the reduction at lower temperature and in shorter period, by the conjoint use of a metal or metals having higher ionization tendency than lead in the reaction system. Examples of these metals are aluminum, iron, nickel, tin, cobalt or magnesium. These metals can be used singly or in mixture of at least two of them. The metals to be used are not limited in shape and may be selected from a wide forms such as powder, plate, foil, bulk or needle. Powdery metal is preferably used in order to proceed the reaction smoothly. The particle size of powdery metal is selected from a wide range but is preferably about 10 to 300 mesh. The amount of the metal to be used having higher ionization tendency than lead is usually about 1.0 to 50 moles atom, preferably about 1.0 to 5 moles atom per mole atom of the carbinol derivative of the formula (I).

In case of using the metal having higher ionization tendency than lead, it is possible to use a lead compound in place of metal lead.

The above lead compound may be one containing lead having a valency of zero, two or four. Further, these compounds may be in the form of a hydrate. As the lead compound, conventionally known compounds are widely used. Examples thereof are lead fluoride, lead chloride, lead bromide, lead iodide or like lead halide, lead nitrate, lead sulfate, lead perchlorate, lead borate, lead carbonate, lead phosphate or like lead salt of inorganic acid, lead acetate, lead oxalate, lead stearate or like lead salt of aliphatic acid, lead oxide, lead hydroxide, or chelates of lead having a valency of zero, 2 or 4. Examples of ligands for the chelate are ethylenediamine tetraacetic acid, nitrilotriacetic acid or like chelating agent, carbonyl compound, carboxylic acid or like oxygen-containing compound, amine, oxime, ammonia, nitrile or like nitrogen compound, organic phosphine or like phosphorus compound, etc. These lead compounds can be used singly or in mixture of at least two of them. Although only one molecule of lead or lead compound is theoretically required, the amount thereof to be used is usually about 0.00001 to 0.5 mole, preferably about 0.0001 to 0.2 mole per mole of the starting carbinol derivative of the formula (I).

The present reduction reaction is conducted in an organic solvent or aqueous organic solvent, when required with addition of an acid. Organic solvents are selected from a wide range of compounds which dissolve the compound of the formula (I) are not reduced in the reaction condition. Examples thereof are methanol, ethanol, propanol, isopropanol, butanol, tert-butanol or like alcohol, formic acid, acetic acid, propionic acid or like lower carboxylic acid, tetrahydrofuran, dioxane, methyl cellosolve, dimethoxyethane or like ether, acetonitrile, dimethylformamide or dimethylacetamide. These solvent can be used singly or in mixture of at least two of them, and may contain water as required. The amount of the solvent is usually about 0.5 to 150l, preferably about 1 to 20l per kg of the compound of the formula (I).

As an acid used as required in the invention are used inorganic acids and organic acids ranging from strong acid to weak acid. Examples thereof are hydrochloric acid, sulfuric acid, nitric acid, perchloric acid, hydrobromic acid, hydroiodic acid, hydrofluoric acid, bromous acid, bromic acid, hypochlorous acid, hypobromous acid, phosphoric acid, phosphorous acid, boric acid, silicic acid or like mineral acid, formic acid, acetic acid, propionic acid, oxalic acid, tartaric acid, benzoic acid, malic acid, malonic acid, monochloroacetic acid, dichloroacetic acid, trichloroacetic acid, trifluoroacetic acid or like carboxylic acid, benzenesulfonic acid, toluene-sulfonic acid, naphthalenesulfonic acid, methanesulfonic acid, trifluoromethanesulfonic acid, chlorosulfonic acid or like sulfonic acid, benzenesulfinic acid, toluenesulfinic acid or like sulfinic acid, ascorbic acid, Meldrum's acid, Squaric acid, pyromeconic acid, lower alkyl ester of malonic acid, lower alkyl ester of acetylacetic acid, phenol, cresol, barbituric acid or like acidic compound, etc., or a salt of the acid and a base which is weaker in basicity than a conjugated base thereof.

The reaction temperature depends on the kinds of starting material, solvent, etc., but is usually about 0° to 150° C., preferably about 20° to 100° C. After completion of the reaction, the reaction mixture is for example concentrated and extracted to obtain the desired 1,1-disubstituted ethylene derivative of the formula (II) in almost pure form. Further, the derivative can be purified as required by distillation, recrystallization, column chromatography or like usual means.

The present invention has the following advantages by finding lead is an excellent reducing agent.

1. 1,1-Disubstituted ethylene derivative can be prepared in extremely high selectivity and yield without requiring a further purification.

2. The present desired compound can be prepared with use of an easily available equipment and with a simple procedure without a special apparatus.

3. Generally, strict limitations are demanded in view of public pollution for coducting a reaction which uses a heavy metal as a reagent in industrial scale. In the present invention, it is possible to reduce the amount of lead or lead compound to an extremely small amount by conjoint use of a metal which has no pollution problem, and to make easy the treatment of the reaction waste.

As stated above, the present invention provides an extremely advantageous method in industrial scale of preparing 1,1-disubstituted ethylene derivative.

The present invention will be described in greater detail with reference to examples.

EXAMPLE 1

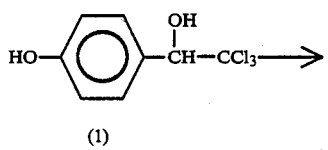

(1)

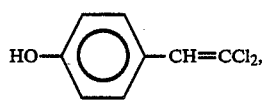

(2)

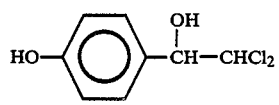

(3)

To a round bottom flask equipped with a condenser were added 1.21 g (5 mmole) of Compound (1), 8 ml of methanol, 5 g of 50% sulfuric acid and 4.14 g (20 mmole) of lead powder (280mesh) and the mixture was stirred under reflux condition for 5 hours. After completion of the reaction, the reaction mixture was concentrated at a reduced pressure and the resulting residue was extracted with ethyl acetate after addition of 10 ml of water. The extract was washed with saturated aqueous solution of sodium bicarbonate, dried on anhydrous magnesium sulfate and concentrated to give 1.05 g of white crystal. By gas chromatography (GC) analysis, by-product, Compound (3) was produced less than 0.1%. Purification with use of silicagel column gives 902 mg (yield 96%) of Compound (2) as a white crystal. The NMR spectrum was consistent with the structure.

NMR(CDCl$_3$): δ 5.02(s,1H,OH), 6.73(s,1H,—CH=), 6.73(m,2H,Ph), 7.40(m,2H,Ph).

EXAMPLES 2 to 8

The reactions were conducted in the same manner as in Example 1 with the exception of using the reaction conditions listed in Table 1 and various solvents were used in place of methanol. Table 1 also shows yields of the obtained para-hydroxy-β,β-dichloro-styrenes.

TABLE 1

| Ex. | Solvent | (ml) | Temp (°C.) | Time (Hr) | Yield (%) |
|---|---|---|---|---|---|
| 2 | 20% aqueous methanol | (8) | 65 | 4 | 95 |

TABLE 1-continued

| Ex. | Solvent | (ml) | Temp (°C.) | Time (Hr) | Yield (%) |
|---|---|---|---|---|---|
| 3 | Ethanol | (8) | 65 | 12 | 93 |
| 4 | Acetic acid | (8) | 65 | 12 | 91 |
| 5 | 20% aqueous acetic acid | (8) | 65 | 6 | 95 |
| 6 | 20% aqueous THF | (8) | 65 | 6 | 90 |
| 7 | DMF | (8) | 70 | 5 | 91 |
| 8 | 50% aqueous acetonitrile | (8) | 55 | 5 | 92 |

THF: Tetrahydrofuran
DMF: Dimethylformamide

EXAMPLES 9 to 13

The reactions were conducted in the same manner as in Example 1 with the exception of using the reaction conditions listed in Table 2 and various acids were used in place of 50% of sulfuric acid. Table 2 also shows yields of the obtained para-hydroxy-β,β-dichlorostyrenes.

TABLE 2

| Ex. | Acid | (ml) | Temp (°C.) | Time (Hr) | Yield (%) |
|---|---|---|---|---|---|
| 9 | 35% HCl | (1.5) | 65 | 5 | 96 |
| 10 | p-Toluenesulfonic acid | (2) | 65 | 12 | 94 |
| 11 | Acetic acid | (5) | reflux | 24 | 90 |
| 12 | Trichloroacetic acid | (5) | reflux | 24 | 92 |
| 13 | 75% H$_3$PO$_4$ | (2) | reflux | 12 | 89 |

EXAMPLES 14

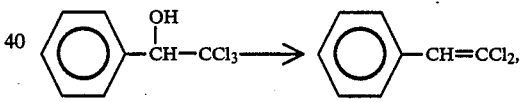

(4)                          (5)

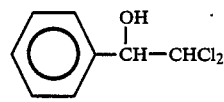

(6)

To a round bottom flask equipped with a condenser were added 2.26 g (10 mmole) of Compound (4), 5 ml of methanol, 2.66 g of 35% hydrochloric acid, 6 mg (0.028 mmole) of lead powder (280mesh) and 378 mg (14 mmole) of aluminum powder (100mesh) and the mixture was stirred at 65° C. for 5 hours. After completion of the reaction, the reaction mixture was treated in the same manner as in Example 1 and concentrated to give 1.75 g of colorless transparent oil. By gas chromatography (GC) analysis, by-product, Compound (6) was produced less than 0.1%. Purification with use of silicagel column gives 1.65 g (yield 95%) of Compound (5) as colorless transparent oil. The NMR spectrum was consistent with the structure.

NMR(CDCl$_3$): δ 6.82(s,1H,—CH=), 7.09~7.59(m,5H,Ph).

EXAMPLES 15 to 20

The reactions were conducted in the same manner as in Example 14 with the exception of using the reaction conditions listed in Table 3 and various lead compounds were used in place of lead powder. Table 3 also shows yields of the obtained β,β-dichlorostyrenes.

TABLE 3

| Ex. | Lead compound | (mg) | Temp (°C.) | Time (Hr) | Yield (%) |
|---|---|---|---|---|---|
| 15 | $PbCl_2$ | (8) | 65 | 4 | 96 |
| 16 | $PbSO_4$ | (10) | 65 | 6 | 90 |
| 17 | $Pb(OAc)_2 \cdot 3H_2O$ | (11) | 65 | 5 | 95 |
| 18 | $Pb(OAc)_4$ | (13) | 65 | 5 | 94 |
| 19 | PbO | (20) | 65 | 5 | 90 |
| 20 | $Pb_2O(OH)_2$ | (15) | 65 | 6 | 91 |

EXAMPLES 21

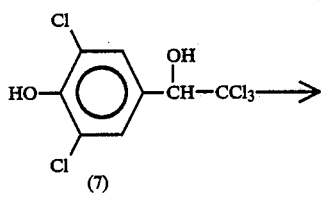
(7)

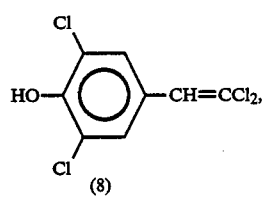
(8)

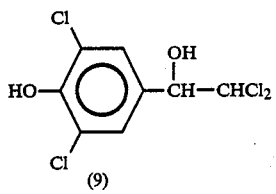
(9)

To a round bottom flask equipped with a condenser were added 3.11 g (10 mmole) of Compound (7), 6 ml of methanol, 3.4 g of 35% hydrochloric acid, 15 mg (0.072 matom) of lead powder and 460 mg (17 mmole) of aluminum powder and the mixture was stirred at 65° C. for 5 hours. The reaction mixture was treated in the same manner as in Example 1 to give 2.66 g of pale yellow crystal. By gas chromatography (GC) analysis, by-product, Compound (9) was produced less than 0.1%. Purification with use of silicagel column gives 2.36 g (yield 92%) of Compound (8). The NMR spectrum was consistent with the structure.

NMR($CDCl_3$): δ 5.90(s,1H,OH), 6.64(s,1H,—CH=), 7.44(s,2H,Ph).

EXAMPLES 22 to 43

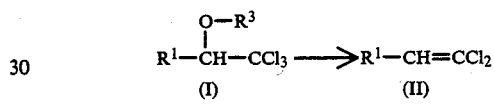

The reactions were conducted in the same manner as in Example 21 with use of the starting materials lised in Table 4. Products lised in Table 4 were obtained in high yields and selectivities.

TABLE 4

| EX. | Starting material | Product |
|---|---|---|
| 22 | Br, HO—C$_6$H$_2$(Br)—CH(OH)—CCl$_3$ | Br, HO—C$_6$H$_2$(Br)—CH=CCl$_2$ |
| 23 | Cl, Cl—C$_6$H$_3$(Cl)—CH(OH)—CCl$_3$ | Cl, Cl—C$_6$H$_3$(Cl)—CH=CCl$_2$ |
| 24 | methylenedioxy-C$_6$H$_3$—CH(OH)—CCl$_3$ | methylenedioxy-C$_6$H$_3$—CH=CCl$_2$ |
| 25 | Ph—CH$_2$O—C$_6$H$_4$—CH(OH)—CCl$_3$ | Ph—CH$_2$O—C$_6$H$_4$—CH=CCl$_2$ |
| 26 | NC—C$_6$H$_4$—CH(OH)—CCl$_3$ | NC—C$_6$H$_4$—CH=CCl$_2$ |

4,886,891

TABLE 4-continued

| EX. | Starting material | Product |
|---|---|---|
| 27 | naphthyl-CH(OH)-CCl$_3$ | naphthyl-CH=CCl$_2$ |
| 28 | (CH$_3$)$_2$CH-CH(OH)-CCl$_3$ | (CH$_3$)$_2$CH-CH=CCl$_2$ |
| 29 | (CH$_3$)$_2$C=CH-CH(OH)-CCl$_3$ | (CH$_3$)$_2$C=CH-CH=CCl$_2$ |
| 30 | 4-CH$_3$-C$_6$H$_4$-CH(OAc)-CCl$_3$ | 4-CH$_3$-C$_6$H$_4$-CH=CCl$_2$ |
| 31 | 4-AcO-C$_6$H$_4$-CH(OAc)-CCl$_3$ | 4-HO-C$_6$H$_4$-CH=CCl$_2$ |
| 32 | 4-HO-C$_6$H$_4$-CH(OCH$_3$)-CCl$_3$ | 4-HO-C$_6$H$_4$-CH=CCl$_2$ |
| 33 | 2-(1-hydroxy-2,2,2-trichloroethyl)cyclohexanone | 2-(2,2-dichlorovinyl)cyclohexanone |
| 34 | C$_6$H$_5$-CO-CH(CH$_3$)-CH(OH)-CCl$_3$ | C$_6$H$_5$-CO-CH(CH$_3$)-CH=CCl$_2$ |
| 35 | β-lactone with CCl$_3$ substituent | HOOC-CH$_2$-CH=CCl$_2$ |
| 36 | CH$_2$=C(CH$_3$)-CH$_2$-CH(OH)-CCl$_3$ | CH$_2$=C(CH$_3$)-CH$_2$-CH=CCl$_2$ |
| 37 | cyclooctenyl-CH(OH)-CCl$_3$ | cyclooctenyl-CH=CCl$_2$ |
| 38 | 2-methylcyclohexenyl-CH(OH)-CCl$_3$ | 2-methylcyclohexenyl-CH=CCl$_2$ |

TABLE 4-continued

| EX. | Starting material | Product |
|---|---|---|
| 39 | CH₃-C(=C(CH₃))-CH₂-O-CH(CCl₃) (cyclic) | (CH₃)₂C=C(CH₃)-... CH₂OH, CH=CCl₂ |
| 40 | 3-methylphenyl-O-CH(OAc)-CCl₃ | 3-methylphenyl-O-CH=CCl₂ |
| 41 | 3,4-dihydroxyphenyl-CH(OH)-CCl₃ | 3,4-dihydroxyphenyl-CH=CCl₂ |
| 42 | HOCH₂-CH(OH)-CH(OH)-CCl₃ | HOCH₂-CH(OH)-CH=CCl₂ |
| 43 | EtOOC-cyclopropyl(gem-diMe)-CH(OH)-CCl₃ | EtOOC-cyclopropyl(gem-diMe)-CH=CCl₂ |

EXAMPLE 44

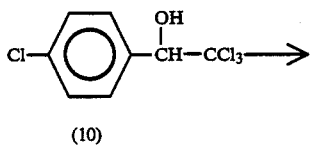

(10)

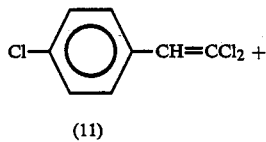

(11)

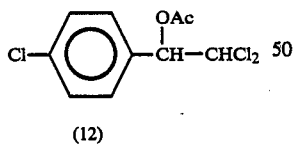

(12)

To a round bottom flask were added 184 mg (0.5 mmole) of lead bromide and 150 mg (5.5 mmole) of finely cut aluminum foil. Thereto were added 10 ml of dimethyl-formamide and 1.51 g (5 mmole) of Compound (10) and the mixture was stirred at room temperature for 3.5 hours. After completion of the reaction, the reaction mixture was extracted with ethyl acetate after addition of 10 ml of water. The extract was washed with saturated aqueous solution of sodium bicarbonate and saturated aqueous solution of sodium chloride, dried on anhydrous magnesium sulfate and concentrated to give 1.0 g of pale yellow crystal. By GC analysis, by-product, Compound (12) was produced less than 0.1%. Purification with use of silicagel column gives 880 mg (yield 84%) of Compound (11) as a white crystal. The NMR spectrum was consistent with the structure.

NMR(CDCl₃): δ 6.68(s,1H,—CH=), 7.1~7.5(m,4H,Ph).

EXAMPLES 45 to 53

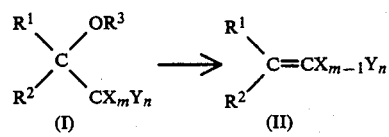

$$R^1R^2C(OR^3)(CX_mY_n) \longrightarrow R^1R^2C=CX_{m-1}Y_n$$

(I)      (II)

The reactions were conducted in the same manner as in Example 44 with use of the starting materials listed in Table 5. Products listed in Table 5 were obtained in high yields and selectivities.

TABLE 5

| EX. | Starting material | Product |
|---|---|---|
| 45 | 4-Cl-phenyl-CH(OAc)-CBr₃ | 4-Cl-phenyl-CH=CBr₂ |

TABLE 5-continued

| EX. | Starting material | Product |
|---|---|---|
| 46 | Cl-C6H4-CH(OAc)-CCl2COOCH3 | Cl-C6H4-CH=C(COOCH3)(Cl) |
| 47 | Cl-C6H4-CH(OAc)-CCl2CONH2 | Cl-C6H4-CH=C(CONH2)(Cl) |
| 48 | Cl-C6H4-CH(OAc)-CCl2CN | Cl-C6H4-CH=C(CN)(Cl) |
| 49 | (CH3)2C=CH-CH(OAc)-CBr3 | (CH3)2C=CH-CH=CBr2 |
| 50 | EtOOC-cyclopropyl-CH(OAc)-CCl3 | EtOOC-cyclopropyl-CH=CCl2 |
| 51 | EtOOC-cyclopropyl-CH(OAc)-CBr3 | EtOOC-cyclopropyl-CH=CBr2 |
| 52 | EtOOC-cyclopropyl-CH(OAc)-CCl2COOCH3 | EtOOC-cyclopropyl-CH=C(Cl)(COOCH3) |
| 53 | EtOOC-cyclopropyl-CH(OAc)-CCl2CN | EtOOC-cyclopropyl-CH=C(Cl)(CN) |

EXAMPLE 54

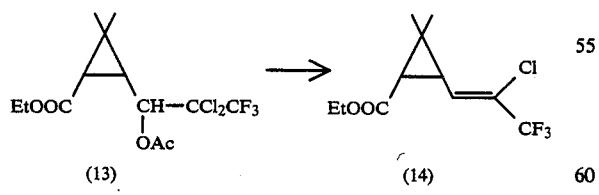

(13) → (14)

To a round bottom flask were added 184 mg (0.5 mmole) of lead bromide and 162 mg (6.0 mmole) of finely cut aluminum foil. Thereto were added 10 ml of dimethyl-formamide and 1.83 g (5 mmole) of Compound (13) and the mixture was stirred at room temperature for 10 hours. After completion of the reaction, the reaction mixture was extracted with ethyl acetate after addition of 10 ml of water. The extract was washed with saturated aqueous solution of sodium bicarbonate and saturated aqueous solution of sodium chloride, dried on anhydrous magnesium sulfate and concentrated to give 1.4 g of pale yellow liquid. Purification with use of silicagel column gives 1.25 g (yield 92%) of Compound (14) as a colorless liquid. The NMR spectrum was consistent with the structure.

$^1$H-NMR(CDCl$_3$): δ  1.14~1.44(m,9H,CH$_3$—C), 1.75(d,1H,H—C—CO), 2.23~2.55(m,1H,HC—C=C), 4.18(q,2H,CH$_3$—O), 6.12(d,1H,H—C=C).

EXAMPLE 55

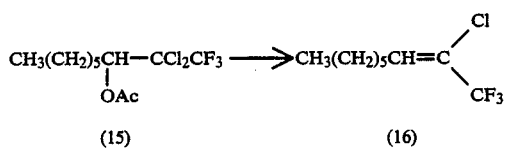

To a round bottom flask were added 184 mg (0.5 mmole) of lead bromide and 162 mg (6.0 mmole) of finely cut aluminum foil. Thereto were added 10ml of dimethyl-formamide and 1.55 g (5 mmole) of Compound (15) and the mixture was stirred at room temperature for 10 hours. After completion of the reaction, the reaction mixture was extracted with ethyl acetate after addition of 10 ml of water. The extract was washed with saturated aqueous solution of sodium bicarbonate and saturated aqueous solution of sodium chloride, dried on anhydrous magnesium sulfate and concentrated to give 900 mg of pale yellow liquid. Purification with use of silicagel column gives 773 mg (yield 72%) of Compound (16) as a colorless liquid. The NMR spectrum was consistent with the structure.

$^1$H-NMR(CDCl$_3$): $\delta$ 0.87(t,3H,CH$_3$), 1.10~1.75(m,8H,CH$_2$), 2.00~2.55(m,2H,CH$_2$—C=C), 6.37(t,1H,—CH=C).

We claim:

1. A process for preparing a 1,1-disubstituted ethylene derivative of the formula

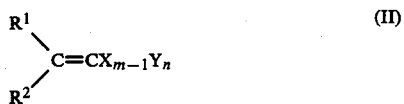

which comprises reacting lead with a carbinol derivative of the formula

wherein $R^1$ and $R^2$ are same or different, substituted or unsubstituted and are each hydrogen, $C_1$–$C_{10}$ straight-chain or branched-chain alkyl, $C_1$–$C_{10}$ straight-chain or branched-chain alkyl having 1 to 3 CH$_2$ groups replaced with —CO—, $C_3$–$C_{10}$ alicyclic, $C_3$–$C_{10}$ alicyclic having at least one side chain having 1 to 5 carbons, $C_2$–$C_{10}$ straight-chain or branched-chain unsaturated hydrocarbon, aryl, heterocyclic, aralkyl or aryloxy and $R^1$ and $R^2$ taken together may form a ring, $R^3$ is hydrogen atom, $C_1$–$C_5$ straight-chain or branched-chain alkyl, substituted or unsubstituted aryl, aralkyl having a substituted or unsubstituted aryl, acyl or —(CH$_2$)$_j$— bonded to $R^1$ in one terminal, J–D$_{25}$, a part of —(CH$_2$)$_j$— group is —CO—, X and Y are same or different and are fluorine, chlorine, bromine or iodine atom, m and n are an integer of 1 to 2, m+n=3, and when m is 2, Y is fluorine, chlorine, bromine, iodine, further hydrogen, carboxy, protected carboxyl, amido, cyano or trifluoromethyl, said reaction being conducted in an organic solvent or aqueous organic solvent for said carbinol derivative, and using about 1.0 to 10 moles atom of lead per mole atom of the carbinol derivative.

2. A process as defined in claim 1 wherein $R^1$ and $R^2$ contain substituents selected from the group consisting of hydroxyl, protected hydroxyl, acyl, acyloxy, halogen, aralkyl, amino, amino substituted with $C_1$–$C_5$ straight-chain or branched-chain alkyl, protected amino, nitro, protected thiol, carboxyl, protected carboxyl, formyl, protected formyl, sulfonic acid, protected sulfonic acid and cyano.

3. A process for preparing a 1,1-disubstituted ethylene derivative of the formula

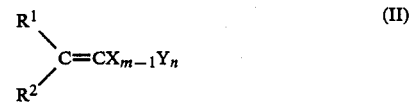

which comprises reacting lead or lead compound containing lead having a valence of zero, two or four with a carbinol derivative of the formula

in the presence of a method having higher ionization tendency than lead, wherein $R^1$ and $R^2$ are same or different, substituted or unsubstituted and are each hydrogen, $C_1$–$C_{10}$ straight-chain or branched-chain alkyl, $C_1$–$C_{10}$ straight-chain or branched-chain alkyl having 1 to 3 CH$_2$ groups replaced with —CO—, $C_3$–$C_{10}$ alicyclic, $C_3$–$C_{10}$ alicyclic having at least one side chain having 1 to 5 carbons, $C_2$–$C_{10}$ straight-chain or branched-chain unsaturated hydrocarbon, aryl, heterocyclic, aralkyl or aryloxy and $R^1$ and $R^2$ taken together may form a ring, $R^3$ is hydrogen atom, $C_1$–$C_5$ straight-chain or branched-chain alkyl, substituted or unsubstituted aryl, aralkyl having a substituted or unsubstituted aryl, acyl or —(CH$_2$)$_j$— bonded to $R^1$ in one terminal, j=0~5, a part of —(CH$_2$)$_j$— group is —CO—, X and Y are same or different and are fluorine, chlorine, bromine or iodine atom, m and n are an integer of 1 to 2, m+n=3, and when m is 2, Y is fluorine, chlorine, bromine, iodine, further hydrogen, carboxy, protected carboxyl, amido, cyano or trifluoromethyl, said reaction being conducted in an organic solvent or aqueous organic solvent for said carbinol derivative, and using about 1.0 to 10 moles atom of lead per mole atom of the carbinol derivative.

4. A process as defined in claim 3 wherein the metal having higher ionization tendency than lead is aluminum, iron, nickel, tin, cobalt, magnesium or a mixture thereof.

5. A process as defined in claim 4 wherein the metal having higher ionization tendency than lead is aluminum.

6. A process as defined in claim 3 wherein the lead or lead compound is used in an amount of about 0.0001 to 0.5 mole per mole of the carbinol derivative of the formula (I).

7. A process as defined in claim 3 wherein the metal having higher ionization tendency than lead is used in an amount of about 1.0 to 50 moles atom per mole atom of the carbinol derivative of the formula (I).

8. A process according to claim 1 wherein $R^1$ and $R^2$ taken together form a ring containing a heteroatom.

* * * * *